(12) United States Patent
Jones

(10) Patent No.: US 10,434,263 B2
(45) Date of Patent: Oct. 8, 2019

(54) PIERCE EAR HOLE PROTECTOR

(71) Applicant: Joseph Jones, Brooklyn, NY (US)

(72) Inventor: Joseph Jones, Brooklyn, NY (US)

( * ) Notice: Subject to any disclaimer, the term of this patent is extended or adjusted under 35 U.S.C. 154(b) by 145 days.

(21) Appl. No.: 15/722,991

(22) Filed: Oct. 2, 2017

(65) Prior Publication Data

US 2018/0369502 A1    Dec. 27, 2018

Related U.S. Application Data

(60) Provisional application No. 62/604,140, filed on Jun. 24, 2017.

(51) Int. Cl.
*A61M 5/32* (2006.01)
*A47K 7/00* (2006.01)
*A61M 5/315* (2006.01)

(52) U.S. Cl.
CPC ...... *A61M 5/3291* (2013.01); *A61M 5/31511* (2013.01); *A61M 2005/31518* (2013.01); *A61M 2210/0662* (2013.01)

(58) Field of Classification Search
CPC ............ A61M 5/3291; A61M 5/31511; A61M 3/0262; A61M 2210/0662; A61M 2005/3104; A61F 11/006
See application file for complete search history.

(56) References Cited

U.S. PATENT DOCUMENTS

| | | | |
|---|---|---|---|
| 6,047,209 A * | 4/2000 | Denny | A61M 5/282 604/21 |
| 10,105,019 B2 * | 10/2018 | Moore | A47K 7/00 |
| 2004/0089022 A1 * | 5/2004 | Ashton | A44C 15/0035 63/12 |
| 2013/0006289 A1 * | 1/2013 | Harper | A44C 7/001 606/188 |

* cited by examiner

*Primary Examiner* — Daniel J Colilla

(57) ABSTRACT

The Pierce Ear Hole Protector is an Earrings that is a hypodermic tube with holes on it and goes in the hole of a pierce ear to inject a healing substance to keep a pierce ear from closing or getting infected or sore by a administering a injection to the center of the tube treating area around pierce ear hole with a medicine of choice for healing and pain relief.

4 Claims, 5 Drawing Sheets

PIERCE EAR HOLE PROTECTOR

BACKGROUND OF THE INVENTION

U.S. Pat. No. 2,752,764 relates to an interchangeable ornament earring

U.S. Pat. No. 3,176,475A relates to an adjustable clip for earring having a single tooth thread means. U.S. Pat. No. 2,824,474A relates to a tool for adjusting earring and similar devicr.

SUMMARY OF THE INVENTION

The present invention relates to an earring, a pierce ear hole protector earring;
wherein a metal, gold metallic hypodermic tube, that go into a hole of a pierce ear;
wherein an injection of a healing substance around said pierce ear hole area to keep said pierce ear hole from a closing happening or getting an infection or a sore;
an administering an injection into an center hole of said hypodermic tube;
treating said sore area around said pierce ear hole with a medicine of choice for a pain relief and an healing.
1. It is an object of the present invention to comprise a hypodermic tube with a hole in a top upper area of said hypodermic tube wherein at said top of hypodermic tube; said hole is near a funnel shape cup to treat said pierce ear hole area.
2. It is an object of the present invention for said hypodermic tube; to comprise a small funnel shape cup with a hole in center of said cup on a top end of said hypodermic tube; wherein the cup is connected to said hypodermic tube.
3. It is an object of the present invention for said hypodermic tube to comprise an sequence of several small holes on an bottom or opposite end of the hypodermic tube;
for allowing a slow injection.
4. It is an object of the present invention to comprise a metal/rubber or plastic cap that screw on or Snap-On over said small funnel shape cup.
5. It is an object of the present invention for said cap to comprise a plunger;
with a designer head on the center of said cap to make an injection of a substance;
into said cup into a center hole of hypodermic tube.
6. It is an object of the present invention for said small funnel shape cup connected to said hypodermic tube; to hold an ointment like Vaseline or Neosporin or other ointment; wherein then deposit an injection of ointment to a center top hole of hypodermic tube for a pain relief.
7. It is an object of the present invention to comprise a small screw on nipple;
on opposite end of said hypodermic tube; wherein said nipple is configure to drawing or absorb a fluid substance; like alcohol or hydrogen peroxide or other fluids into nipple then screw nipple on said other end of hypodermic tube; then squeeze nipple to inject a fluid into said center of said hypodermic tube.

BRIEF DESCRIPTION OF THE INVENTION

Figure 1:
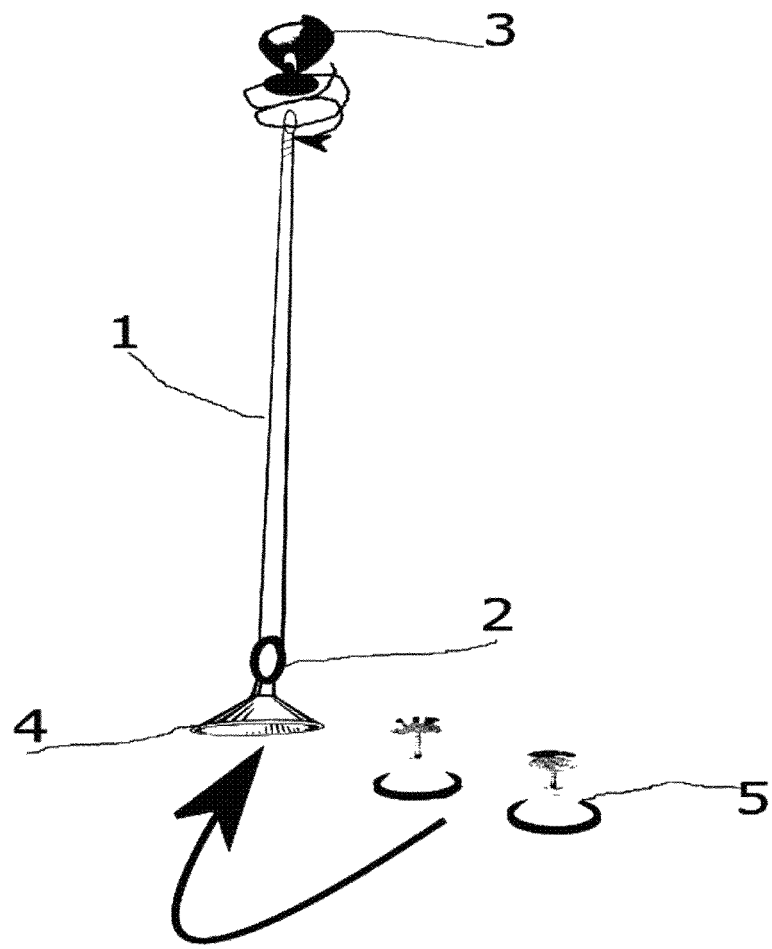
Figure 2:
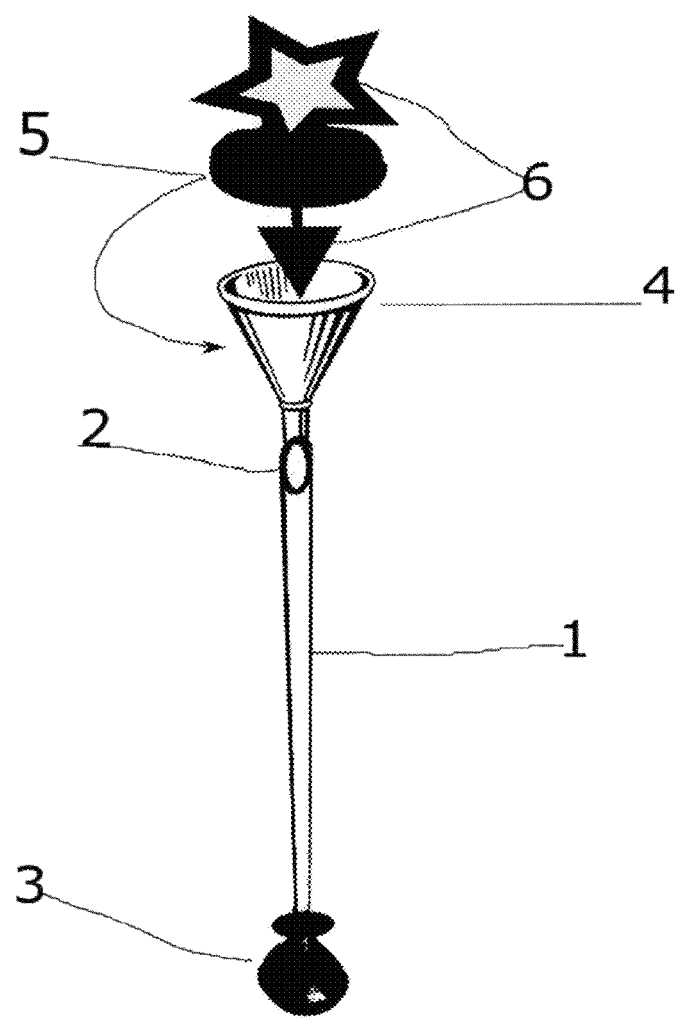
Figure 3:
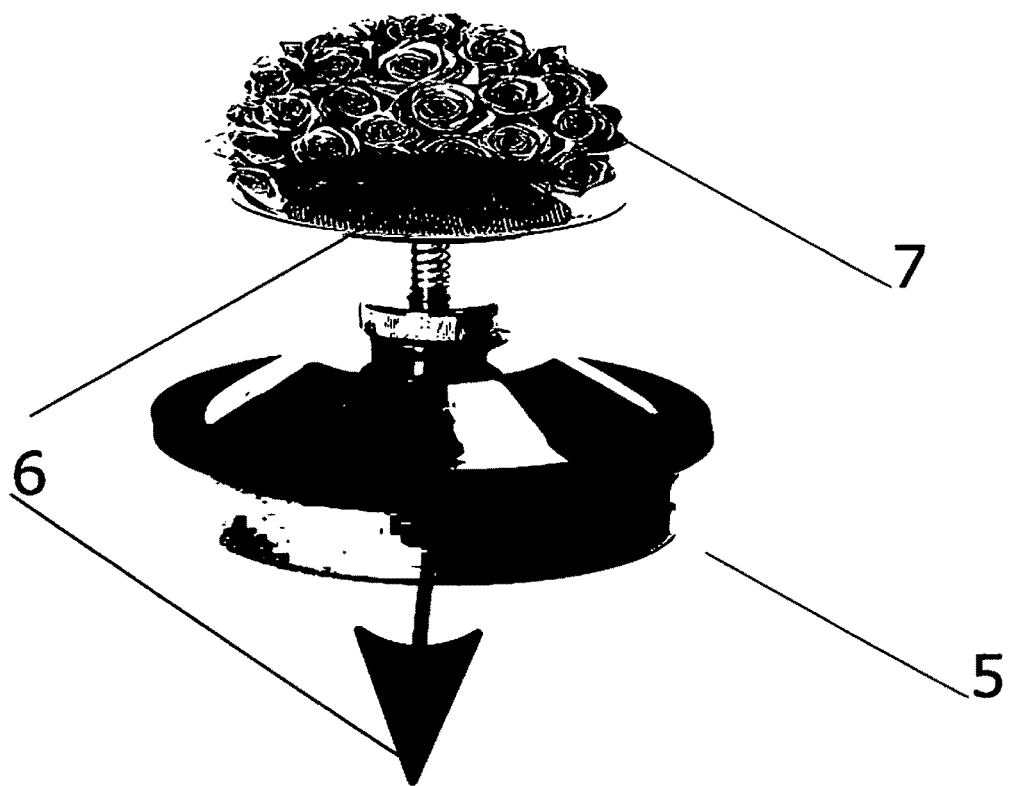
Figure 4:
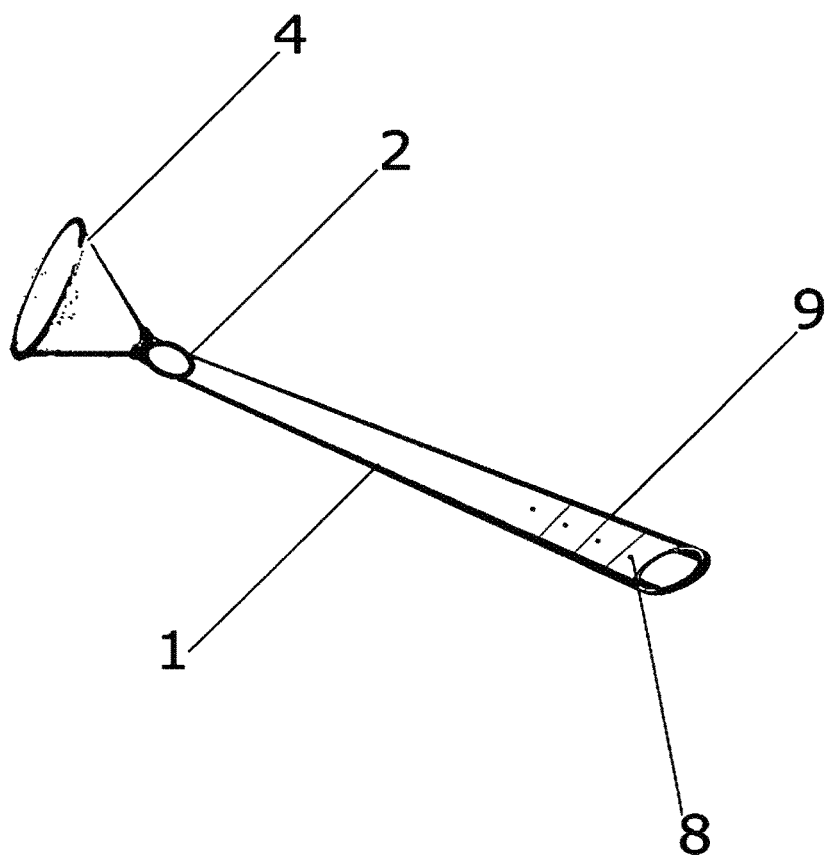
Figure 5:
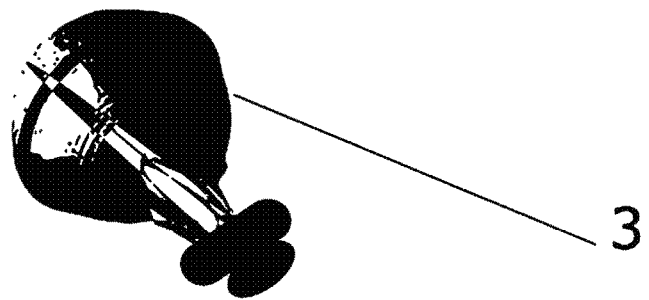

FIG. 1 illustrates the bottom to the top, or the back to the front view of the present invention.
FIG. 2 illustrates the top to the bottom, or the front to the back view of the present invention.
FIG. 3 illustrates the cap with a designer head plunger that goes over the front funnel shape to cover the present invention.
FIG. 4 illustrates the hypodermic tube with funnel shape head and holes, of the present invention.
FIG. 5 illustrates a small screw on nipple that goes on the back of the hypodermic tube of the present invention.

DETAIL DESCRIPTION

FIG. 1 illustrates the back to the front
1. Hypodermic tube
2. Hole in hypodermic tube
3. Screwing on nipple
4. Funnel shape cup
5. Two caps with plunger and designer head
FIG. 2 illustrates the front to the back
1. Hypodermic tube
2. Hole in hypodermic tube
3. Nipple on the end of hypodermic tube
4. funnel head cup
5. cap going on funnel cup
6. plunger and designer head (a star)
FIG. 3 illustrates the cap with plunger and designer head
5. is the cap
6. plunger
7. design (roses)
FIG. 4 illustrates hypodermic tube funnel head cup hole small holes and screw lines
1. hypodermic tube
2. hole under funnel head
4. funnel head
8. small holes on the end of hypodermic tube
9. screw lines
FIG. 5 illustrates the screw on nipple that go on the end of hypodermic tube
3. screw on nipple

The invention claimed is:
1. A pierce ear hole protector comprising:
a hypodermic tube with a small funnel shape cap on a first end of the hypodermic tube with a hole in center of said funnel cup;
a hole near the first end of said hypodermic tube near said funnel shape cup;
a sequence of small holes near a second end of said hypodermic tube;
a cap including a little designer head plunger in a center of said cap, wherein said cap is configured to be screwed on or snapped on to said funnel shape cup;
and a small nipple configured to be screwed on to the second end of said hypodermic tube.
2. The pierced ear hole protector of claim 1, further comprising:
a healing substance deposited in said funnel shape cup, wherein said hypodermic tube is configure to be inserted in hole of pierced ear,
wherein the pierced ear hole protector is configured to administer an injection of said healing substance to the hole in the top end of said hypodermic tube to keep said pierce ear hole from closing or getting an infection or sore by said administration of said injection thereby treating an area around a pierced ear hole with said healing substance.
3. The pierced ear hole protector of claim 1, wherein said small screw on nipple is configured to be screwed onto the second end of said hypodermic tube over said sequence of small holes and is configured to allow a slow injection of a healing fluid such as alcohol, hydrogen peroxide or another fluid to the area around said pierced ear hole.

4. The pierced ear hole protector of claim 1, wherein said small screw on nipple is configured to draw-in or absorb a healing fluid and then inject said healing fluid into the hole near the first end of said hypodermic tube by squeezing the small nipple, wherein the injection of said healing fluid is administered into said hypodermic tube and out of the hole near the first end of the hypodermic tube.

* * * * *